United States Patent
Hunter et al.

(10) Patent No.: US 6,585,772 B2
(45) Date of Patent: Jul. 1, 2003

(54) METHOD OF SURFACE OXIDIZING ZIRCONIUM AND ZIRCONIUM ALLOYS AND RESULTING PRODUCT

(75) Inventors: Gordon Hunter, Memphis, TN (US); Catherine M. Asgian, Minnetonka, MN (US); Gary L. Hines, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 13 days.

(21) Appl. No.: 09/909,612

(22) Filed: Jul. 20, 2001

(65) Prior Publication Data

US 2002/0042656 A1 Apr. 11, 2002

Related U.S. Application Data

(63) Continuation-in-part of application No. 09/381,271, filed as application No. PCT/US98/06059 on Mar. 27, 1998, now Pat. No. 6,447,550.
(60) Provisional application No. 60/042,364, filed on Mar. 27, 1997.

(51) Int. Cl.$^7$ .................................................. A61F 2/28
(52) U.S. Cl. .................................................. 623/23.54
(58) Field of Search ........................ 623/23.54, 23.55, 623/23.53, 23.52, 23.5, 23.15, 22.4, 20.14, 18.11

(56) References Cited

U.S. PATENT DOCUMENTS

| | | | | |
|---|---|---|---|---|
| 5,037,438 A | * | 8/1991 | Davidson | .................... 623/18 |
| 5,152,794 A | | 10/1992 | Davidson | |
| 5,180,394 A | | 1/1993 | Davidson | |
| 5,316,594 A | * | 5/1994 | Kemp | ........................ 148/281 |
| 5,370,694 A | | 12/1994 | Davidson | |
| 5,372,660 A | | 12/1994 | Davidson et al. | |
| 5,496,359 A | | 3/1996 | Davidson | |
| 5,562,730 A | | 10/1996 | Davidson | |
| 6,447,550 B1 | * | 9/2002 | Hunter et al. | ............ 623/22.15 |

* cited by examiner

*Primary Examiner*—Corrine McDermott
*Assistant Examiner*—Alvin Stewart
(74) *Attorney, Agent, or Firm*—Fulbright & Jaworski L.L.P.

(57) ABSTRACT

A coating of blue-black or black oxidized zirconium of uniform and controlled thickness on a zirconium or zirconium alloy material is accomplished through the use of a single phase crystalline material substrate having an altered surface roughness. An oxidized zirconium coating of uniform and controlled thickness is especially useful on orthopedic implants of zirconium or zirconium-based alloys to provide low friction, highly wear resistant surfaces on artificial joints, such as, but not limited to, hip joints, knee joints, shoulders, elbows, and spinal implants. The uniformly thick oxidized zirconium surface of controlled depth on prostheses provide a barrier against implant corrosion caused by ionization of the metal prostheses. The invention is also useful in non-articulating implant devices such as bone plates, bone screws, etc.

10 Claims, 1 Drawing Sheet

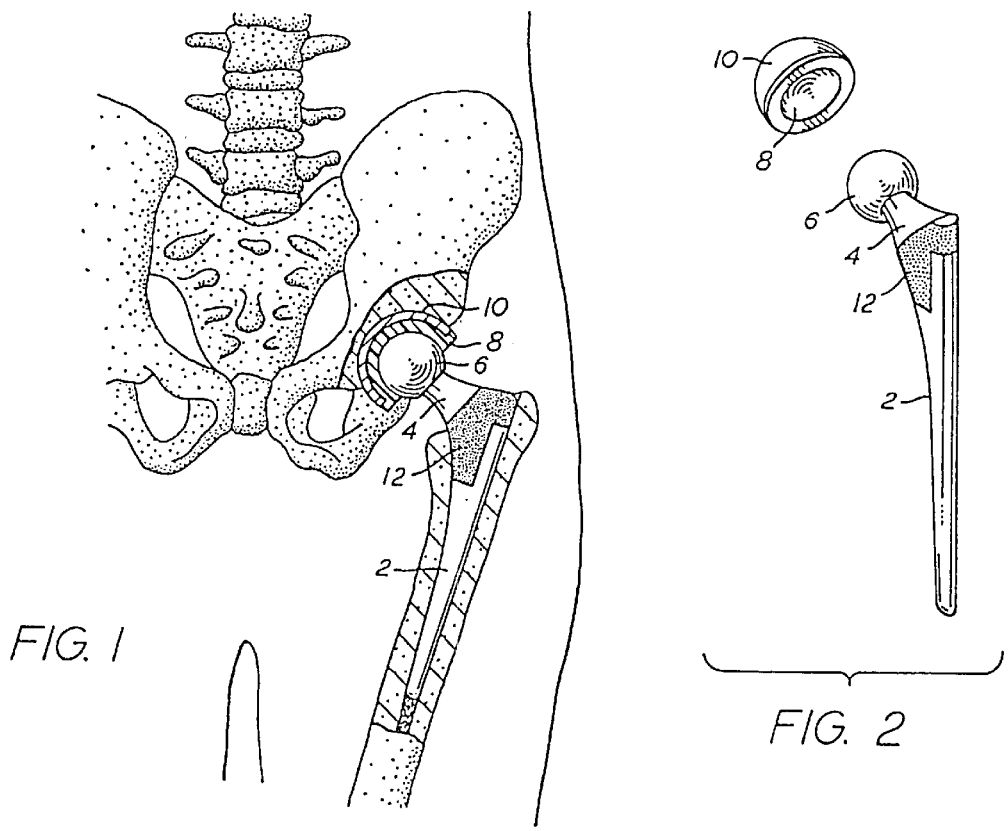
FIG. 1
FIG. 2
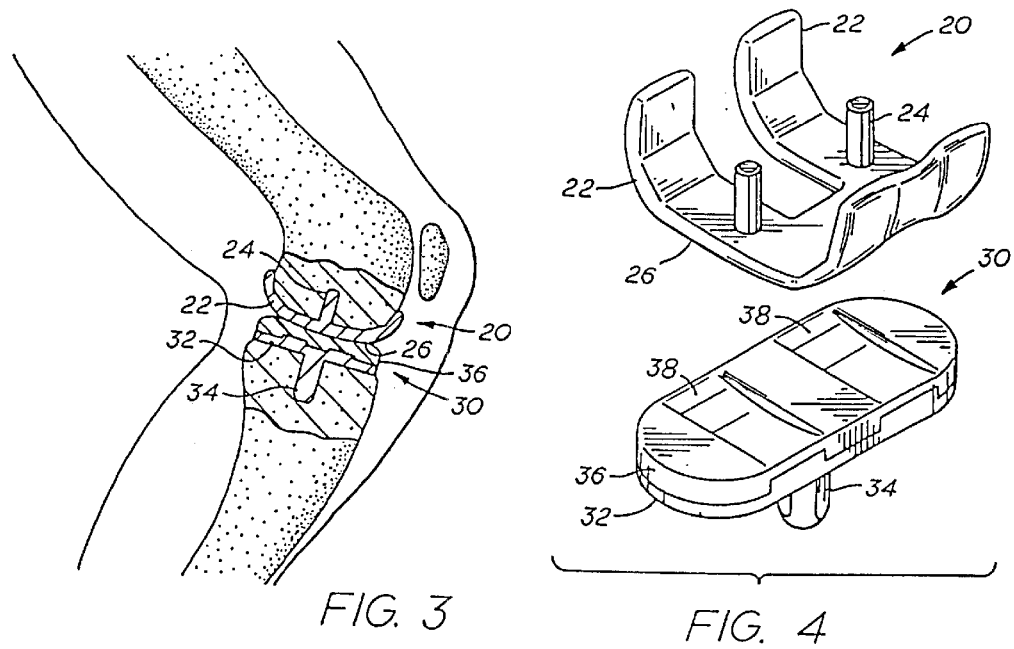
FIG. 3
FIG. 4

METHOD OF SURFACE OXIDIZING ZIRCONIUM AND ZIRCONIUM ALLOYS AND RESULTING PRODUCT

This application is a continuation-in-part of U.S. application Ser. No. 09/381,271, filed Nov. 24, 1999, now U.S. Pat. No. 6,447,550 B1, which is a United States National Stage of International Application No. PCT/US98/06059, filed Mar. 27, 1998, and claims priority to U.S. Provisional Application Ser. No. 60/042,364, filed Mar. 27, 1997, (which are hereby incorporated by reference for all purposes).

BACKGROUND OF THE INVENTION

This invention relates to metallic implants with load bearing surfaces coated with a thin, dense, low friction, highly wear-resistant, uniformly thick coating of oxidized zirconium.

The invention also relates to uniformly thick oxidized zirconium coatings on the non-load bearing surfaces of an orthopedic implant where the oxidized zirconium provides a barrier between the metallic prosthesis and body tissue thereby preventing the release of metal ions and corrosion of the implant.

The invention also relates to a method of producing a uniformly thick oxide coating on zirconium or a zirconium alloy by controlling the surface roughness of the zirconium or zirconium alloy having a single phase crystalline structure and uniform composition prior to formation of the oxide coating.

The excellent corrosion resistance of zirconium has been known for many years. Zirconium displays excellent corrosion resistance in many aqueous and non-aqueous media and for this reason has seen an increased use in the chemical process industry and in medical applications. A limitation to the wide application of zirconium in these areas is its relatively low resistance to abrasion and its tendency to gall. This relatively low resistance to abrasion and the tendency to gall is also demonstrated in zirconium alloys.

Orthopedic implant materials must combine high strength, corrosion resistance and tissue compatibility. The longevity of the implant is of prime importance especially if the recipient of the implant is relatively young because it is desirable that the implant function for the complete lifetime of a patient. Because certain metal alloys have the required mechanical strength and biocompatibility, they are ideal candidates for the fabrication of prostheses. These alloys include 316L stainless steel, chrome-cobalt-molybdenum alloys and, more recently, titanium alloys which have proven to be the most suitable materials for the fabrication of load-bearing prostheses.

One of the variables affecting the longevity of load-bearing implants, such as hip joint implants, is the rate of wear of the articulating surfaces and long-term effects of the metal ion release. A typical hip joint prosthesis includes a stem, a femoral head and an acetabular cup against which the femoral head articulates. Wear of either or both of the articulating surfaces results in an increasing level of wear particulates and "play" between the femoral head and the cup against which it articulates. Wear debris can contribute to adverse tissue rejection leading to bone resorption, and ultimately the joint must be replaced.

The rate of wear is dependent upon a number of factors which include the relative hardness and surface finish of the material which constitute the femoral head and the acetabular cup, the frictional coefficient between the materials of the cup and head, the load applied and the stresses generated at the articulating surface. The most common material combinations currently used in fabrication of hip joints implants include femoral heads of cobalt or titanium alloys articulating against acetabular cups lines with organic polymers or composites of such polymers including, e.g., ultra high molecular weight polyethylene (UHMWPE), and femoral heads of polished alumina in combination with acetabular cups lined with an organic polymer or composite or cups made of polished alumina.

Of the factors that influence the rate of wear of conventional hip-joint implants, the most significant are patient weight and activity level. Additionally, heat which is generated by friction in the normal use of the implant as, for instance, in walking has been shown to cause accelerated creep and wear of the polyethylene cup. Furthermore, there is a correlation between the frictional moment which transfers torque loading to the cup and the frictional coefficient between the femoral head and the surface of the acetabular cup against which the head articulates. Cup torque has been associated with cup loosening. Thus, in general, the higher the coefficient of friction for a given load, the higher the level of torque generated. Ceramic bearing surfaces have been shown to produce significantly lower levels of frictional torque.

It is also noteworthy that two of the three commonly used hip-joint systems as indicated above include a metallic femoral head articulating against a UHMWPE liner inside the acetabular cup. UHMWPE, being a polymeric material, is more susceptible to creep when heated than the commonly used metal alloys or ceramics and is consequently more susceptible to wear than the alloys or ceramics.

It has also been found that metal prostheses are not completely inert in the body. Body fluids act upon the metals causing them to slowly corrode by an ionizing process that thereby releases metal ions into the body. Metal ion release from the prosthesis is also related to the rate of wear of load bearing surfaces because the passive oxide film, which is formed on the surface, is constantly removed. The repassivation process constantly releases metal ions during the ionizing process. Furthermore, the presence of third-body wear (cement or bone debris) accelerates this process and microfretted metal particles increase friction. Consequently, the UHMWPE liner inside the acetabular cup, against which the femoral head articulates, is subjected to accelerated levels of creep, wear and torque.

U.S. Pat. No. 4,145,764 to Suzuki, et al. recognizes that while metal prostheses have excellent mechanical strength they tend to corrode in the body by ionization. Suzuki, et al. also recognized the affinity between ceramics and bone tissue but noted that ceramic prostheses are weak on impact resistance. Suzuki, et al therefore proposed a metal prosthesis plasma sprayed with a bonding agent which is in turn covered with a porous cement coating which will allow the ingrowth of bone spincules into the pores. This combination, it was said, would provide both the mechanical strength of metals and the bio-compatibility of ceramics.

The Suzuki patent did not address the issue of friction or wear of orthopedic implant bearing surfaces but confined itself to the single issue of the biocompatibility of metal prostheses. Furthermore, Suzuki et al. did not address the issue of dimensional changes that occur when applying a coating or the effect of these dimensional changes in the tightness of fit between the surfaces of an articulating joint prosthesis.

In addition, the application of ceramic coating to metal substrates often results in non-uniform, poorly adhering coatings which tend to crack due to the differences in elastic modulus or thermal expansion between the ceramic and underlying metal substrate. Furthermore, such coatings tend to be relatively thick (50–300 microns) and since the bond between the metal and the ceramic coating is often weak, there is the risk of galling or separation of ceramic coatings.

Previous attempts have been made to produce oxidized zirconium coatings on zirconium parts for the purpose of increasing their abrasion resistance. One such process is disclosed in U.S. Pat. No. 3,615,885 to Watson which discloses a procedure for developing thick (up to 0.23 mm) oxide layers on Zircaloy 2 and Zircaloy 4. However, this procedure results in significant dimensional changes especially for parts having a thickness below about 5 mm, and the oxide film produced does not exhibit especially high abrasion resistance.

U.S. Pat. No. 2,987,352 to Watson discloses a method of producing a blue-black oxide coating on zirconium alloy parts for the purpose of increasing their abrasion resistance. Both U.S. Pat. Nos. 2,987,352 and 3,615,885 produce a zirconium dioxide coating on zirconium alloy by means of air oxidation. U.S. Pat. No. 3,615,885 continues the air oxidation long enough to produce a beige coating of greater thickness than the blue-black coating of U.S. Pat. No. 2,987,352. This beige coating does not have the wear resistance of the blue-black coating and is thus not applicable to many parts where there are two work faces in close proximity. The beige coating wears down more quickly than the blue-black oxide coating with the resulting formation of oxidized zirconium particles and the loss of the integrity of the oxidized zirconium surface. With the loss of the oxide surface the zirconium metal is then exposed to its environment and can lead to transport of zirconium joints away from the surface of the metal into the adjacent environment.

The blue-black coatings have a thickness which is less than that of the beige coating although the hardness of the blue-black coating is higher than that of the beige coating. This harder blue-black oxide coating lends itself better to surfaces such as prosthetic devices. Although the blue-black coating is more abrasion resistant than the beige coating it is a relatively thin coating. It is therefore desirable to produce the blue-black coatings of increased abrasion resistance without producing the same type coatings of the prior art.

U.S. Pat. No. 5,037,438 to Davidson discloses a method of producing zirconium alloy prostheses with a oxidized zirconium surface. U.S. Pat. No. 2,987,352 to Watson discloses a method of producing zirconium bearings with a oxidized zirconium surface. The oxide coating produced is not always uniform in thickness and the non-uniformity reduces the integrity of the bonding between the zirconium alloy and the oxide layer and the integrity of the bonding within the oxide layer. Both U.S. Pat. Nos. 2,987,352 and 5,037,438 are incorporated by reference as though fully set forth herein.

In the international publication, PCT WO 98/42390, and its related, pending U.S. application Ser. No. 09/381,217, Hunter, et al. described a method for obtaining an oxidized zirconium coating of uniform thickness. Hunter taught that such is obtained by applying pre-oxidation treatment techniques to the substrate material that result in a refined microstructure and an altered surface roughness. Microstructure refinement is taught in PCT WO 98/42390 by techniques which include the hot forge conversion of ingot to wrought barstock, closed die forging, rapid solidification, and powder consolidation. The altered surface roughness is accomplished by processes such as grinding, buffing, mass finishing, vibratory finishing, among others. U.S. application Ser. No. 09/381,217 is incorporated by reference as though fully set forth herein.

There exists a need for a method to produce oxide coatings of uniform thickness on zirconium alloys. There exists a need for a metal alloy based orthopedic implant having low friction and highly wear resistant load bearing surfaces that can be implanted for the lifetime of the recipient. There also exists a need for a metal alloy based orthopedic implant that is not prone to corrosion by the action of the body fluids and is biocompatible and stable over the lifetime of the recipient.

The instant invention provides an improved method for forming a uniformly thick oxide coating on zirconium or a zirconium alloy, each having a single phase crystalline structure and uniform composition, by inducing an altered surface roughness on single phase/single composition zirconium based substrate, prior to oxidizing the zirconium or zirconium alloy to form a blue-black oxidized zirconium coating of uniform and controlled thickness. The invention also provides a method for forming a uniformly thick oxide coating on a zirconium or zirconium alloy prosthesis, for implantation in a patient, by inducing an altered surface roughness on at least a portion of the zirconium or zirconium alloy prosthesis, wherein the zirconium or oxidized zirconium consists, at least in part, of a single phase crystalline structure and uniform composition, prior to oxidizing the prosthesis to form a blue-black oxidized zirconium coating of uniform and controlled thickness on at least a portion of the surface of the prosthesis.

SUMMARY OF THE INVENTION

As used herein, "a" or "an" may mean one or more. As used herein in the claim(s), when used in conjunction with the word "comprising", the words "a" or "an" may mean one or more than one. As used herein, "another" may mean at least a second or more.

As used herein, the term "single phase crystalline structure and uniform composition" is defined as an alloy or a pure metallic material having a homogeneous, solid solution and a microstructure with only one crystalline phase. In the case of an alloy, it refers to a single, homogeneous, solid solution in which the overall material consists of only one crystalline phase.

As used herein, "zirconium alloy" is defined as any metal alloy containing zirconium in any amount greater than zero. Thus, an alloy in which zirconium is a minor constituent is considered a "zirconium alloy" herein.

The following discussion contains illustrations and examples of preferred embodiments for practicing the present invention. However, they are not limiting examples. Other examples and methods are possible in practicing the present invention.

The invention provides a zirconium or zirconium-containing metal alloy prosthesis or implant coated, at least in part, via in situ oxidation with a uniformly thick blue-black or black layer of oxidized zirconium and a method of forming the aforementioned uniform coating. The uniform coating of oxidized zirconium provides the prosthesis with a thin, dense, low friction, wear resistant, biocompatible surface ideally suited for use on articulating surfaces of joint prostheses wherein a surface or surfaces of the joint articulates, translates, or rotates against mating joint surfaces which are also coated with oxidized zirconium. The uniform oxidized zirconium coating may therefore be usefully employed on the femoral heads or inside surfaces of acetabular cups of hip-joint implants or on the articulating surfaces of other types of prostheses, such as but not limited to knee, shoulder or elbow joints or spinal implants.

In one embodiment, a method of producing a uniform coating of blue-black or black oxidized zirconium on a zirconium or zirconium alloy includes the steps of altering the surface roughness of a zirconium or zirconium alloy having a single phase crystalline structure and uniform composition and subsequently oxidizing said zirconium or zirconium alloy. In a specific embodiment, the step of altering the surface roughness may be accomplished using an abrasive surface preparation process comprising a grinding step, although other surface roughening steps such as buffing, mass finishing, and vibratory finishing may be used. In the preferred embodiment, the surface is roughened to a surface roughness (Ra) of from about 3 microinches to 25 microinches, preferably, this range is 3.5 microinches to 7 microinches. A grain size of less than ASTM micro-grain size number 10 is preferred. In the preferred embodiment, the oxidation process uses air as an oxidant, although other suitable oxidants, such as oxygen, may be alternatively used. The preferred single phase crystalline structure and uniform composition useful in the present invention is alpha-phase zirconium with about 0.3 wt % of oxygen. Alternatively, pure alpha-phase zirconium may be used. The preferred embodiment uses a zirconium or zirconium alloy useful in the present invention is produced by hot forge conversion of ingot to barstock. Alternatively, one may use closed die forging, rapid solidification, or powder consolidation for the production of the zirconium or zirconium alloy.

In another embodiment of the present invention, a knee prosthesis for implantation in a patient, includes a prosthesis body formed of zirconium or zirconium alloy which has an implant portion for inserting into the body tissue of the patient, a bearing surface comprising at least one condyle on the prosthesis body, a tibial component formed of an organic polymer or polymer based composite and adapted to cooperate with the bearing surface, and a coating of blue-black or black oxidized zirconium of uniform thickness prepared by the method described above for forming a uniform coating of oxidized zirconium directly on the bearing surface of the condyle portion for reducing wear of the organic polymer or polymer-based composite component. In a specific embodiment, the thickness of the oxidized zirconium coating is up to about 20 microns. Alternatively, this thickness is up to about 10 microns. In a specific embodiment, the prosthesis further includes an irregular surface structure adapted to accommodate tissue ingrowth on a portion of the prosthesis body. In another embodiment, the irregular surface structure is formed of zirconium or zirconium alloy beads attached to the outer surface of the prosthesis body, wherein at least a portion of the surface of the beads is oxidized to blue-black or black oxidized zirconium. Another embodiment includes an irregular surface structure formed of zirconium or zirconium alloy wire mesh connected to the outer surface of the prosthesis body, wherein at least a portion of the surface of the mesh is oxidized to blue-black or black oxidized zirconium.

In another embodiment of the present invention a hip prosthesis, for implantation in a patient, includes a prosthesis body for implantation into a femur comprising a head portion formed of zirconium or zirconium alloy, a bearing surface on the head portion of the prosthesis body, an acetabular cup having an inner surface formed of an organic polymer or a polymer-based composite, the inner surface being adapted to cooperate with the bearing surface on the head portion, and a coating of blue-black or black oxidized zirconium of uniform thickness prepared by the method described above for forming a uniform coating of oxidized zirconium directly on the bearing surface of the head portion for reducing wear of the acetabular cup inner surface. In a specific embodiment, the thickness of the oxidized zirconium coating is up to about 20 microns. Preferably, this thickness is up to about 10 microns. In a specific embodiment, the prosthesis body further includes an irregular surface structure adapted to accommodate tissue ingrowth on a portion of the prosthesis body. In a specific embodiment, the irregular surface structure is formed of zirconium or zirconium alloy beads connected to the outer surface of the prosthesis body, wherein at least a portion of the surface of the beads is oxidized to blue-black or black oxidized zirconium. In yet another specific embodiment, a prosthesis of having an irregular surface structure is formed of zirconium or zirconium alloy wire mesh connected to the outer surface of the prosthesis body, wherein at least a portion of the surface of the mesh is oxidized to blue-black or black oxidized zirconium.

In another embodiment of the present invention, a prosthesis for implantation in a patient includes a prosthesis body formed of zirconium or zirconium alloy comprising an implant portion for insertion into the body tissue of the patient, a bearing surface on the prosthesis body, the bearing surface being sized and shaped to engage or cooperate with a second bearing surface on another prosthesis portion, the second bearing surface being formed of an organic polymer or polymer-based composite and a coating of blue-black or black oxidized zirconium of uniform thickness prepared by the method described above for forming a uniform coating of oxidized zirconium, the coating having a thickness of up to about 20 microns on the bearing surface of the prosthesis body for reducing wear on the organic polymer or polymer-based second bearing surface of said another prosthesis portion. In an alternative embodiment, the coating has a thickness of up to about 10 microns. In a specific embodiment for a hip joint having a head portion as a bearing surface, the other prosthesis portion is an acetabular cup, with the head portion being adapted to cooperate with the inner surface of the acetabular cup, said inner surface comprising an organic polymer or polymer-based composite. In a specific embodiment for a knee joint, the bearing surface of the prosthesis body includes at least one condyle, and the other prosthesis portion comprises a tibial component formed of an organic polymer or polymer-based composite, with at least one condyle being adapted to cooperate with the tibial component. Any of these embodiments have specific embodiments where the prosthesis body comprises an irregular surface structure adapted to accommodate tissue ingrowth on a portion of the prosthesis body. In a specific embodiment of the irregular surface structure prosthesis, the irregular surface structure is formed of zirconium or zirconium alloy beads connected to the outer surface of the prosthesis body with at least a portion of the surface of the beads is oxidized to blue-black or black oxidized zirconium. In another specific embodiment, the irregular surface structure is formed of zirconium or zirconium alloy wire mesh connected to the outer surface of the prosthesis body with at least a portion of the surface of the mesh is oxidized to blue-black or black oxidized zirconium.

In another embodiment, a prosthesis for implantation in a patient, includes a prosthesis body formed of zirconium or zirconium alloy comprising an implant portion for inserting into the body tissue of the patient, a bearing surface on the prosthesis body, a counter-bearing surface formed of an organic polymer or polymer-based composite and adapted to cooperate with the bearing surface, and a coating of blue-black or black oxidized zirconium uniform thickness, prepared by the method described above for forming a uniform coating of oxidized zirconium, directly on the bearing surface for reducing wear of the organic polymer or polymer-based composite counter-bearing surface. In a specific embodiment, the thickness of the oxidized zirconium coating is up to about 20 microns. Preferably, this thickness is up to about 10 microns. In a specific embodiment, the prosthesis body further comprises an irregular surface structure adapted to accommodate tissue ingrowth on a portion of the prosthesis body. In a specific embodiment, the irregular surface structure is formed of zirconium or zirconium alloy beads connected to the outer surface of the prosthesis body, wherein at least a portion of the surface of the beads is oxidized to blue-black or black oxidized zirconium. In yet another specific embodiment, a prosthesis of having an irregular surface structure is formed of zirconium or zirconium alloy wire mesh connected to the outer surface of the prosthesis body, wherein at least a portion of the surface of the mesh is oxidized to blue-black or black oxidized zirconium.

In another embodiment of the invention, a prosthesis for implantation in a patient includes a prosthesis body having an external surface at least a portion of which is formed of zirconium or zirconium alloy, each having single phase crystalline structure and uniform composition and an altered surface roughness, a blue-black or black oxidized zirconium coating of uniform thickness formed on the aforementioned portion of the external surface by inducing an altered surface roughness on at least that portion of the external surface and subjecting that portion of the external surface of the prosthesis body to an oxidation process. In a specific embodiment, the prosthesis body is an endoprosthesis body. In specific embodiments of the endoprosthesis body, the endoprosthesis can be a knee joint, hip joint, or shoulder joint. It may also comprise a spinal implant. In a specific embodiment, the thickness of the oxidized zirconium coating is up to about 20 microns. Preferably, this thickness is up to about 10 microns. In a specific embodiment of the endoprosthesis body invention, the prosthesis body further includes an irregular surface structure adapted to accommodate tissue ingrowth on a portion of the prosthesis body. In a specific embodiment, the irregular surface structure is formed of zirconium or zirconium alloy beads connected to the outer surface of the prosthesis body, wherein at least a portion of the surface of the beads is oxidized to blue-black or black oxidized zirconium. In yet another specific embodiment, a prosthesis which has an irregular surface structure is formed of zirconium or zirconium alloy wire mesh connected to the outer surface of the prosthesis body, wherein at least a portion of the surface of the mesh is oxidized to blue-black or black oxidized zirconium.

In another embodiment of the present invention, a non-articulating medical implant formed at least in part of zirconium or zirconium alloy material includes a partial or complete coat of blue-black or black oxidized zirconium of uniform thickness prepared by the method described above for forming a uniform coating of oxidized zirconium. In specific embodiments the medical implant is a bone plates or a bone screws.

DESCRIPTION OF THE DRAWINGS

FIG. 1 is a schematic diagram depicting a hip joint prosthesis in position.

FIG. 2 is a schematic diagram showing a typical hip join prosthesis.

FIG. 3 is a schematic diagram of a knee joint prosthesis in place.

FIG. 4 is a schematic diagram of the parts of a typical knee joint.

DETAILED DESCRIPTION OF THE INVENTION

One aspect of the present invention is to provide a method for forming an oxide coating of uniform thickness on zirconium or a zirconium alloy, the zirconium or zirconium alloy each having a single phase crystalline structure and uniform composition and an altered surface roughness. Another aspect of the present invention is to provide a low friction, wear resistant oxide coating of uniform thickness on prosthesis surfaces, such as articulating surfaces and irregular surface structures adapted to accommodate tissue ingrowth on a portion of the prosthesis body.

The subject method of forming an oxide coating of uniform thickness by inducing an altered surface roughness on zirconium or a zirconium alloy, each having a single phase crystalline structure and uniform composition, prior to oxidizing the zirconium or zirconium alloy is applicable to various prosthetic parts and devices. These prosthetic parts and devices include, but are not limited to, cardiovascular implants including heart valves, total artificial heart implants, ventricular assist devices, vascular grafts and stents; electrical signal carrying devices such as pacemaker and neurological leads, and defibrillator leads; guide wires and catheters; percutaneous devices; and joint prostheses including hip joints or surface replacements, knee joints, shoulder joints, elbows, endoprostheses, spinal segments, and fingers. Illustrative examples of such articulating surfaces are shown in the schematic diagrams, FIGS. 1–4. Additionally, applications are possible in non-articulating implant devices such as bone plates, bone screws, etc.

A typical hip joint assembly is shown in situ in FIG. 1. The hip joint stem 2 fits into the femur while the femoral head 6 of the prosthesis fits into and articulates against the inner lining 8 of an acetabular cup 10 which in turn is affixed to the pelvis as shown in FIG. 1. A porous metal bead or wire mesh coating 12 may be incorporated to allow stabilization of the implant by ingrowth of surrounding tissue into the porous coating. Similarly, such a porous metal bead or wire mesh coating can also be applied to the acetabular component. The femoral head 6 may be an integral part of the hip joint stem 2 or may be a separate component mounted upon a conical taper at the end of the neck 4 of the hip joint prosthesis. This allows the fabrication of a prosthesis having a metallic stem and neck but a femoral head of some other material, such as ceramic. This method of construction is often desirable because ceramics have been found to generate less frictional torque and wear when articulating against the UHMWPE lining of an acetabular cup. Additionally, zirconia ceramic has been shown to produce less wear of the UHMWPE than alumina. Regardless of the materials, however, the femoral head articulates against the inner surface of the acetabular cup thereby causing wear and, in the long term, this may necessitate prosthesis replacement. This is especially the case where the femoral head is of metal and the acetabular cup is lined with an organic polymer or composite thereof. While these polymeric surfaces provide good, relatively low friction surfaces and are biocompatible, they are subject to wear and accelerated creep due to the frictional heat and torque to which they are subjected during ordinary use.

While UHMWPE that has been cross-linked through irradiation followed by a hearing step has been shown to exhibit greater wear resistance, it has similar shortcomings. A typical knee joint prosthesis is shown in situ in FIG. 3. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibia platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. While condyles are typically fabricated of metals, the tibial platform may be made from an organic polymer or a polymer-based composite. Thus, the hard metallic condyle surfaces 26 would articulate against a relatively softer organic composition. This may result in wear of the organic material, i.e. the tibial platform, necessitating the replacement of the prosthesis. As in the case of the hip joint, porous bead or wire mesh coatings can also be applied to either the tibial or femoral components of the knee or both.

The invention provides uniformly thick oxidized zirconium coated orthopedic implants or prostheses fabricated of zirconium or zirconium containing metal alloys or a thin coating of zirconium or zirconium alloy on conventional orthopedic implant materials. In order to form continuous and useful oxidized zirconium coatings of uniform thickness over the desired surface of the metal alloy prosthesis substrate, the metal alloy should contain from about 80 to about 100 wt % zirconium, preferably from about 94 to about 100 wt %. Oxygen, and other common alloying elements may be used in the alloy, provided that the resulting alloy be of a single phase. The interstitial elements oxygen, nitrogen, and carbon, among others, have the capability to strengthen zirconium while maintaining a single phase crystalline microstructure. At lower temperatures, zirconium is an alpha ($\alpha$) phase crystal. Beta ($\beta$) phase zirconium is stable at higher temperatures (above about 866° C.) but can become stable at lower temperatures by the addition of $\beta$ stabilizers such as niobium ($\alpha$ stabilizers such as oxygen raise this transition temperature). An example of an alloy useful in the present application is $\alpha$-phase zirconium with 0.3 wt % oxygen, an $\alpha$-phase stabilizer. Other $\alpha$-phase stabilizers include nitrogen, aluminum, and tin. Alternatively, $\beta$-phase zirconium alloyed with one or more $\beta$ stabilizers such as niobium, chromium, iron, and molybdenum are useful in the present invention.

The base zirconium containing metal alloys are fabricated by conventional methods to the shape and size desired to obtain a prosthesis substrate. The shaped zirconium or zirconium alloy must have a single phase crystalline structure and uniform composition such as might be produced by alloying zirconium with one or more other elements to produce a single phase alloy material.

The substrate zirconium or zirconium alloy is then subjected to an abrasive surface preparation process that includes, but is not limited to, grinding, buffing, mass finishing and vibratory finishing. The abrasive surface preparation process is used to induce an altered surface roughness (Ra) of from about 3 microinches to about 25 microinches. Alternatively, the range of surface roughness can be from about 3.5 to about 7 microinches. The appropriate altered surface roughness is induced by altering the pre-existing surface roughness to an altered surface roughness of such a magnitude as to permit the formation of a uniform oxide coating when the zirconium or zirconium alloy, each having a single phase crystalline structure and uniform composition and an appropriately altered surface roughness, is subjected to an oxidation process.

The substrate is then subjected to process conditions which cause the natural (in situ) formation of a tightly adhered, diffusion-bonded coating of uniformly thick oxidized zirconium on its surface. The process conditions include, for instance, air, steam, or water oxidation or oxidation in a salt bath. These processes ideally provide a thin, hard, dense, blue-black or black, low-friction wear-resistant uniformly thick oxidized zirconium film or coating of thicknesses typically on the order of several microns on the surface of the prosthesis substrate. Below this coating, diffused oxygen from the oxidation process increases the hardness and strength of the underlying substrate metal.

The air, steam and water oxidation processes are described in now-expired U.S. Pat. No. 2,987,352 to Watson, the teachings of which are incorporated by reference as though fully set forth. The oxidation process applied to zirconium or a zirconium alloy, each having a single phase crystalline structure and uniform composition and an appropriate degree of altered surface roughness, provides a firmly adherent black or blue-black layer of uniformly thick oxidized zirconium of highly oriented monoclinic crystalline form. If the oxidation is continued to excess, the coating will whiten and separate from the metal substrate. For convenience, the metal prosthesis substrate may be placed in a furnace having an oxygen-containing atmosphere (such as air) and typically heated at 900°–1300° F. for up to about 6 hours. However, other combinations of temperature and time are possible. When higher temperatures are employed, the oxidation time should be reduced to avoid the formation of the white oxide.

One of the salt-bath methods that can be used to apply the oxidized zirconium coatings to the metal alloy prosthesis, is the method of U.S. Pat. No. 4,671,824 to Haygarth, the teachings of which are incorporated by reference as though fully set forth. The salt-bath method provides a similar, slightly more abrasion resistant blue-black or black oxidized zirconium coating. This method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt %. The addition of sodium carbonate lowers the melting point of the salt. As in air oxidation, the rate of oxidation is proportional to the temperature of the molten salt bath and the '824 patent prefers the range of 550°–800° C. (1022°–1470° F.). However, the lower oxygen levels in the bath produce thinner coatings than for furnace air oxidation at the same time and temperature. A salt bath treatment at 1290° for four hours produces an oxide coating thickness of roughly 7 microns.

The overall thickness of the oxidized zirconium coating is primarily controlled by the variables of time and temperature of the in-situ growth process. The instant invention is concerned with the uniformity of thickness of the coating so created. Creation of a uniform oxide coating during the oxidation process, by the here claimed method, is dependent on both a surface with appropriate altered surface roughness and a single phase crystalline structure and uniform composition. The oxide coating initiates and grows from surface asperities, so the oxide initiation sites may be spaced too far apart to produce a uniform coating thickness on a surface that is too smooth. The oxide layer grows by oxygen diffusion along grain boundaries and through microstructural grains. The oxidation rate can be different in grains of different structure and composition (such as between alpha and beta grains in a two-phase zirconium alloy). Thus, the oxide coating may not grow with a uniform thickness through a microstructure that is too coarse. Specific limits for the necessary minimum surface roughness and maximum phase homogeneity can be alloy and application dependent.

The uniformly thick oxidized zirconium coating may range up to about 20 microns. It is preferred that a uniformly thick blue-black oxidized zirconium layer ranging in thickness from about 1 to about 10 microns should be formed. It is most preferred that the uniformly thick oxidized zirconium layer range from about 3 microns to about 7 microns. For example, furnace air oxidation at 1100° F. for 3 hours will form a uniform oxide coating of a thickness of 4–5 microns on a zirconium alloy having greater than 96 wt % zirconium with a surface roughness (Ra) of about 4 microinches. Longer oxidation times and higher oxidation temperatures will increase this thickness, but may compromise coating integrity. For example, one hour at 1300° F. will form an oxide coating thickness of about 9 microns. Of course, because only a thin oxide is necessary on the surface, only very small dimensional changes, typically less than 10 microns over the thickness of the prosthesis, will result. In general, thinner coatings (1–10 microns) have better attachment strength. However, depending upon the application coatings of greater thickness may be used.

Blue-black or black oxidized zirconium coatings produced by any of the prior art methods are quite similar in hardness. For example, if the surface of a wrought zirconium alloy prosthesis substrate is oxidized, the hardness of the surface shows a dramatic increase over the 200 Knoop hardness of the original metal surface. The surface hardness of the blue-black oxidized zirconium surface following oxidation by either salt bath or air oxidation process is approximately 1200–1700 Knoop hardness.

The diffusion-bonded, low friction, highly wear resistant, uniformly thick oxidized zirconium coatings of the present invention can be applied to the surfaces of orthopedic implants subject to conditions of wear and to prosthetic implants and devices requiring a biocompatible surface. Such surfaces include the articulating surfaces of knee joints, elbows and hip joints. As mentioned before, in the case of hip joints, the femoral head and stem are typically fabricated of metal alloys while the acetabular cup may be fabricated from ceramics, metals or organic polymer-lined metals or ceramics.

When the oxidized zirconium coatings are applied to surfaces subject to wear, it is desirable to obtain a smooth finished surface to minimize abrasive wear. After the oxidation process, the oxide coating surface can be polished by any of a variety of conventional finishing techniques. Sufficient oxide thickness must be produced to accommodate the chosen finishing technique. For example, a surface with a uniform oxide coating of about 5 microns thick that had a pre-oxidation surface roughness (Ra) of about 4 microinches can be burnished to a final surface roughness (Ra) of about 2 microinches with a loss of about 1 micron in oxide thickness.

Zirconium or zirconium alloy can also be used to provide a porous bead or wire mesh surface to which surrounding bone or other tissue may integrate to stabilize the prosthesis. These porous coatings can be treated simultaneously by the oxidation of the base prosthesis for the elimination or reduction of metal ion release. Furthermore, zirconium or zirconium alloy can also be used as a surface layer applied over conventional implant materials prior to inducing an altered surface roughness, in situ oxidation and formation of the uniform oxidized zirconium coating.

The process of the present invention avoids the problems of formation of thick oxide coatings of low abrasion resistance and of significant dimensional changes of the process in U.S. Pat. No. 3,615,885. The control of both overall coating thickness and the uniformity of the thickness affords a great deal of dimensional control in the fabrication of prosthetic devices wherein exacting tolerances are required. The present invention also produces an oxide film that is highly abrasion resistant, unlike that of the '885 patent.

The process of the present invention, by inducing an altered surface roughness on zirconium or a zirconium alloy, each having a single phase crystalline structure and uniform composition, results in the formation of a blue-black zirconium dioxide coating of uniform thickness, the depth of which can be controlled by the proper choice of the oxidation conditions. The formation of a uniformly thick oxide coating provides an oxide coating of variable and controlled thickness with especially high abrasion resistance and reduced wear due to high integrity of the adhesion between the oxide layer and the underlying zirconium or zirconium alloy and the high integrity of the adhesion within the oxide layer. The term "high integrity" denotes an oxide coating that is uniform in thickness with no visible cracks or pores when viewed in cross-section by optical microscopy.

The invention provides zirconium or zirconium-containing metal alloy prosthesis with a single phase crystalline structure and uniform composition coated via in situ oxidation with a oxidized zirconium of uniform thickness. The uniformly thick oxidized zirconium coating provides the invention prosthesis with a thin, dense, low friction, high integrity, wear resistant biocompatible surface ideally suited for use on articulating surfaces of joint prosthesis wherein a surface or surfaces of the joint articulates, translates or rotates against mating joint surfaces. The uniformly thick oxidized zirconium coating may therefore be usefully employed on the femoral heads or inside surfaces of acetabular cups of hip-joint implants or on the articulating surfaces of other types of prostheses, such as knee joints.

When a joint surface coated with a uniformly thick oxidized zirconium is employed in a manner wherein it articulates or rotates against a non-metallic or non-oxidized zirconium coated surface, the low friction characteristic and high integrity of the uniformly thick coating causes reduced friction, wear, and heat generation relative to prior art prostheses. This reduced heat generation results in a lowered tendency for the non-metallic or non-oxidized zirconium coating bearing surface to experience creep and torque so that the useful life of the opposing surface is enhanced. Organic polymers, such as UHMWPE, exhibit rapidly increased rates of creep when subjected to heat with consequent deleterious effect on the life span of the liner. Wear debris of the polymer leads to adverse tissue response and loosening of the device. Thus, not only does the uniformly thick oxidized zirconium coating serve to improve the protection of the prosthesis substrate to which it is applied due to its high integrity, it also, as a result of its low friction surface, protects those surfaces against which it is in operable contact and consequently enhances the performance and life of the prosthesis.

A uniformly thick oxidized zirconium coated joint surface also enhances the useful life of the opposing surface when the opposing surface is body tissue. The surgical replacement of one component of the joint is termed "hemiarthroplasty" and because the repaired joint has only one artificial (prosthesis) component, the artificial component is often termed a "unipolar" prosthesis, or "endoprosthesis." The uniformly thick oxidized zirconium coating is a low friction surface for articulation, translation and rotation against body tissue thereby having the same beneficial effect for a body tissue counterface as it does for an organic polymer counterface.

The usefulness of oxidized zirconium coated prosthesis is not limited to load bearing prostheses, especially joints, where a high rate of wear may be encountered. Other applications are possible in non-articulating implant devices such as bone plates, bone screws, etc. Because the uniformly thick oxidized zirconium coating is firmly bonded to the zirconium alloy prosthesis substrate, it provides an enhanced barrier between the body fluids and the zirconium alloy metal thereby preventing the corrosion of the alloy by the process of ionization and its associated metal ion release compared to non-uniform oxide coatings.

Additionally, the natural in situ formation of a uniformly thick oxidized zirconium coating from the presence of zirconium in the substrate metal involves oxygen diffusion into the metal substrate below the oxide coating. Oxygen, an alloying constituent in zirconium, increases the strength of the metal substrate, particularly the fatigue strength. Furthermore, the high integrity of the uniformly thick coating reduces the number of fatigue crack initiation sits relative to a non-uniformly thick oxide coating that contains cracks or pores. Resistance to fatigue loading is paramount in many orthopedic implant applications such as the hip stem, and femoral and tibial knee components. Thus, not only does the formation of the uniformly thick oxidized zirconium coating improve wear, fiction, and corrosion resistance, it also improves the mechanical integrity of the implant device from a strength standpoint.

Although the invention has been described with reference to its preferred embodiments, those of ordinary skill in the art many, upon reading this disclosure, appreciate changes and modifications which may be made and which do not depart from the scope and spirit of the invention as described above or claimed hereafter.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

U.S. Patent Documents:

| | | |
|---|---|---|
| 4,145,764 | March 1979 | Suzuki, et al. |
| 3,615,885 | October 1971 | Watson |
| 2,987,352 | June 1961 | Watson |
| 5,037,428 | August 1991 | Davidson |

Foreign Patent Documents:

| | | |
|---|---|---|
| PCT WO 98/42390 | October 1998 (published) | Hunter et al. |

Other References:

*ASTM Manual on Zirconium and Hafnium*, J. H. Schemel; Special Technical Publication 639, American Society for Testing and Materials, Philadelphia, Pa., 1977.

*Tansformations in Metals*, P. G. Shewmon, McGraw-Hill, New York, 1969.

One skilled in the art readily appreciates that the present invention is well adapted to carry out the objectives and obtain the ends and advantages mentioned as well as those inherent therein. Systems, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

What is claimed is:

1. A method of producing a uniform coating of blue-black or black oxidized zirconium on zirconium or a zirconium alloy, comprising the steps of altering the surface roughness of a zirconium or zirconium alloy having a single phase crystalline structure and uniform composition and subsequently oxidizing said zirconium or zirconium alloy.

2. The method of claim 1 wherein said step of altering comprises altering to a surface roughness (Ra) in the range of about 3 microinches to about 25 microinches.

3. The method of claim 1 wherein said altering step comprises altering to a surface roughness (Ra) in the range of about 3.5 microinches to about 7 microinches.

4. The method of claim 1, wherein said altering step comprises an abrasive surface preparation process comprising:

a step selected from the group consisting of grinding, buffing, mass finishing, and vibratory finishing; or any combination thereof.

5. The method of claim 1, wherein the zirconium or zirconium alloy has a grain size of less than ASTM micrograin size number 10.

6. The method of claim 1, wherein said step of oxidizing comprises the use of air as an oxidant.

7. The method of claim 1, wherein said step of oxidizing comprises the use of oxygen as an oxidant.

8. The method of claim 1, wherein altering step comprises zirconium or a zirconium alloy having about 0.3 percent by weight of oxygen.

9. The method of claim 1 wherein said altering step comprises altering the surface roughness of pure alpha phase zirconium.

10. The method of claim 1, further comprising the step of producing the zirconium or zirconium alloy by a process selected from the group consisting of hot forge conversion of ingot to barstock, closed die forging, rapid solidification and powder consolidation.

* * * * *